United States Patent [19]

Veltrup

[11] Patent Number: 4,690,672
[45] Date of Patent: Sep. 1, 1987

[54] APPARATUS FOR REMOVING SOLID STRUCTURES FROM BODY PASSAGES

[76] Inventor: Elmar M. Veltrup, Hermann-Schumacher-Str. 16a, 4150 Krefeld 1, Fed. Rep. of Germany

[21] Appl. No.: 921,872

[22] Filed: Oct. 21, 1986

Related U.S. Application Data

[63] Continuation of Ser. No. 768,025, Aug. 21, 1985, abandoned.

[30] Foreign Application Priority Data

Sep. 6, 1984 [DE] Fed. Rep. of Germany ... 8426270[U]

[51] Int. Cl.$^4$ ............................................. A61M 3/00
[52] U.S. Cl. ................................................... 604/43
[58] Field of Search ................... 433/95, 96; 128/328, 128/348, 356, 204.25; 604/22, 35, 27, 30, 43–45, 48, 118, 119, 140, 141, 177, 268, 269

[56] References Cited

U.S. PATENT DOCUMENTS

| | | | |
|---|---|---|---|
| 1,902,418 | 3/1933 | Pilgrim | 604/43 |
| 2,147,652 | 2/1939 | Kennison | 128/240 |
| 2,804,075 | 8/1957 | Borden | 604/269 |
| 3,429,313 | 2/1969 | Romanelli | 604/43 |

*Primary Examiner*—C. Fred Rosenbaum
*Assistant Examiner*—J. L. Kruter
*Attorney, Agent, or Firm*—Karl F. Ross; Herbert Dubno

[57] ABSTRACT

A catheter for removing obstructions in a patient has a suction duct connected to a suction pump and with which a pressure duct is associated terminating at a nozzle head of the mouth of the suction duct so that a jet of pressure liquid can be directed into the mouth of the suction duct and against a body held in the mouth via suction applied to the suction duct.

1 Claim, 4 Drawing Figures

APPARATUS FOR REMOVING SOLID STRUCTURES FROM BODY PASSAGES

This is a continuation of co-pending application Ser. No. 768,025 filed on Aug. 21, 1985, now abandoned.

FIELD OF THE INVENTION

My present invention relates to an apparatus or device for the removal of solid material from body passages such as the vasculature, the ducts and passages of the respiratory, digestive and urinary systems, and the like, and specifically the removal of stones, obstructive particles, growths and deposits of tissue or cellular structures.

BACKGROUND OF THE INVENTION

It is known to remove blood thrombi from the vasculature by locally introducing a solvent capable of causing lysis of the thrombus and thereby permitting the fragments to be dissolved or swept away by the circulating blood.

However, there are times when lysis of the thrombus is not possible and there are other solid bodies or structures which form in the vasculature or in other ducts or passages of the human body which must be removed from time to time to prevent obstruction which may be dangerous to the survival of a limb or organ or to the patient. Such materials include calcium residues, tissue structures, blood clots or the like which may obstruct circulation or the release or passage of vital fluids to appropriate locations. With such materials removal has posed a problem.

Other solid objects or deposits, such as kidney stones, gall stones or lime stones, in general to the extent that they cannot be flushed away or dissolved by a solvent, have been destroyed in situ by application of ultrasonic treatment to fragment these stones or deposits, the fragments being then carried away in natural manner. Here too residues are frequently left which may be detrimental in themselves or may serve as nuclei for the generation of new stones or deposits in an accelerated manner.

Mention should be also be made of the fact that the use of catheterization to remove local solid materials has advanced in recent years, it being well known, for example, to provide catheter-like probes capable of excising tissue and inserted through a body aperture and directed to a site from which a biopsy is to be taken or material is to be removed. Such devices may operate with suction.

In spite of the developments in this field in recent years, there nevertheless remains the need for an apparatus which can more fully remove solid materials from the human body and, specifically, from the ducts or passages therein.

OBJECTS OF THE INVENTION

It is, therefore, the principal object of the invention to provide an apparatus which solves this problem, i.e. an apparatus which can more completely remove solid bodies or deposits from the human vasculature or other ducts or passages of the human body.

Yet another object of the invention is to provide an improved method of moving such solids or deposits.

Yet a further object of my invention is to provide an improved apparatus which eliminates drawbacks characterizing earlier techniques for the purposes described.

SUMMARY OF THE INVENTION

These objects and others which will become apparent hereinafter are attained, in accordance with the present invention, by providing a catheter which is open at an end adapted to be fed into a passage of a human body and connected to a suction source in communication with a suction passage of this catheter.

According to the invention, the catheter is provided with a pressure passage as well which is connected to a fluid-pressure source and which terminates in a nozzle at the aforementioned end of the catheter, the nozzle being oriented to direct a jet into the mouth of the suction passage.

For the removal of a blood thrombus, for example, the catheter may be inserted through a vein or other vasculature passage to the site at which the thrombus is located and, by manipulation of the catheter, the thrombus brought into juxtaposition with the mouth of the suction and, at least in part, between this nozzle and the mouth of the suction passage.

When the suction passage is then connected with a vacuum pump, suction draws the thrombus at least in part into the opening constituting the mouth of the suction passage. However, blockage of the mouth of the suction passage is precluded by the high-pressure jet of liquid directed from the nozzle into this mouth which has sufficient force to either drive the thrombus through the suction passage or to break the thrombus apart so that its fragments can be readily drawn through the suction passage. For this purpose, of course, the pressure passage in the catheter is connected with a high-pressure pump.

According to a feature of the invention, the suction passage extends to the free end of the catheter and opens at this free end in the aforementioned mouth, while the nozzle extends from the pressure passage which is parallel. The suction passage partly overhangs this mouth to train the jet back into the latter.

While a portion of the mouth is thus obstructed by the nozzle, the combined effect of the jet and the suction provides a significantly improved ability to remove materials from the vessels of the human body, so that this partial obstructive effect can be ignored. Additionally, both passages can be formed in an integral body with the nozzle so oriented that it promotes passage through the suction duct, i.e. promotes transport of particles into and through the suction duct.

It has been found to be advantageous, especially if the apparatus is to be used for the removal of kidney stones, gall stones and the like, to provide the nozzle so that it is axially shiftable on the catheter relative to the mouth of the suction duct. Thus, for example, the spacing between the nozzle and the mouth of the suction duct can be varied. With a relatively wide spacing, therefore, a gall stone or kidney stone can be worked into position between the nozzle and the mouth of the suction duct so that even large stones can be broken up and the fragments drawn through the suction duct to remove them from the kidney urethra or other portion of the urinary tract or the gall stones can be removed through the bile duct or through other portions of the digestive system. The break-up of larger fragments can be effected in a similar manner. The nozzle can thus be provided on a tube running through the catheter and manipulatable from a location externally of the body.

Because of the small cross section of blood vessels, the catheter should have a cross section which is sufficiently small to enable it to be passed through the vasculature with which it can be used.

For the transport of materials away from a site of implantantion, it has been found to be advantageous to make the flow cross section of the suction passage greater than that of the pressure passage. The pressure fluid should be applied in a pressure of say 30 bar and dimensioned so that the pressure of this fluid to the nozzle, considering losses in the catheter, should be 5 to 20 bar.

Naturally, to regulate the flow conditions in the region of the catheter, pressure regulators can be provided in the suction passage and/or the pressure passage or at the vacuum pump and/or the pressure pump.

So that the material removed from the body can be monitored optically, a sight glass can be provided between the suction passage and the vacuum pump.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
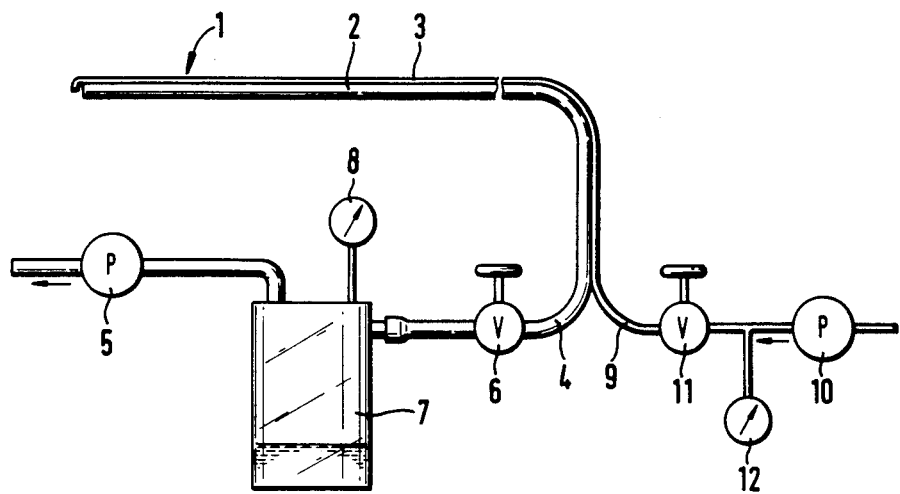
FIG. 1 is a diagrammatic illustration of an apparatus for the removal of blood thrombi from blood vessels according to the invention.
Figure 2:
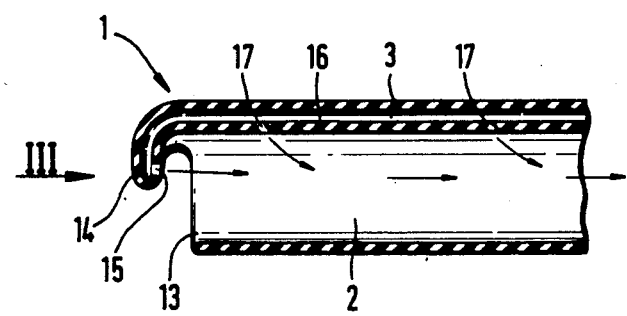
FIG. 2 is a detailed cross section of the end of a catheter of the type shown in FIG. 1.

The apparatus of the invention comprises a catheter 1 with a suction passage 2 and a pressure duct 3 extending parallel to the suction passage 2 and shown to be molded unitarily therewith of a flexible elastomeric material such as a silicon rubber, with at least a free end of the catheter being molded in one piece, as can be seen from FIG. 2, this end being juxtaposed with a thrombus in a blood vessel.

Toward the rear of the catheter, the two ducts may run as separate pipes 4 and 9 to respective pressure control valves 6 and 11, the suction duct being connected via the valve 6 to a receptacle 7 which is transparent to form a sight glass and, via this receptacle, to a suction pump 5. The receptacle 7 also has a pressure gauge 8 to indicate the degree of suction developed in the urethra.

Correspondingly, the pressure control valve 11 of the pressure pipe 9 connects the pressure duct 3 to the fluid pressure pump 10 which can be a high pressure water pump. Between the valve 11 and the pressure pump 10 a pressure gauge 12 can be provided.

The high pressure pump 10 is dimensioned to deliver at least 30 bar of pressure to the fluid applied to duct 3 of the catheter.

Figure 3:
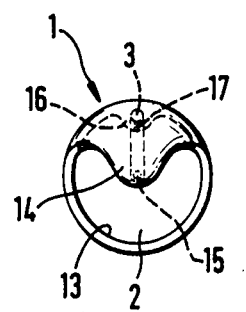
FIG. 3 is an end view of the direction of arrow III of FIG. 2.

As a comparison of FIGS. 2 and 3 will show, the catheter 1 is formed with a mouth 13 of the suction duct 2 at its free end thereof. The cross section of the suction duct 2 is many times greater than the cross section of the pressure passage 3.

A tongue 14 projects beyond the mouth 13 and is turned inward upstream of this mouth and on the inwardly directed underside of this tongue 14, a nozzle aperture 15 is provided so that it trains the jet of pressure fluid into the mouth 13 of the suction duct.

In addition, the common wall 16, separating the pressure duct 3 from the suction duct 2, may be provided with a number of rearwardly directed ports 17 so that additional jets of fluid under pressure are trained in the suction direction along this duct to increase the suction effect and to drive solid particles through the suction duct away from the mouth 13 of the latter. Arrows are provided in FIG. 2 to show the flow direction of the jet of pressure fluid which can be pulsed if desired.

The catheter 1 is fed through a blood vessel and manipulated, e.g. under fluoroscope, until the end of the catheter lies directly ahead of the thrombus. A suction pump 5 is then turned on to draw the thrombus at least partly in the opening 13. The pressure pump 10 is then turned on so that the jets of the pressure liquid drive the thrombus into the suction duct and/or break up the thrombus so that its fragments are drawn through the suction duct assisted by the jets from the orifices 17.

The latter jets may further break up the thrombus.

The valves 6 and 11 allow the pressure relationships to be established to suit any condition which may arise and the sight glass 7 allows visually monitoring of the effect.

Figure 4:
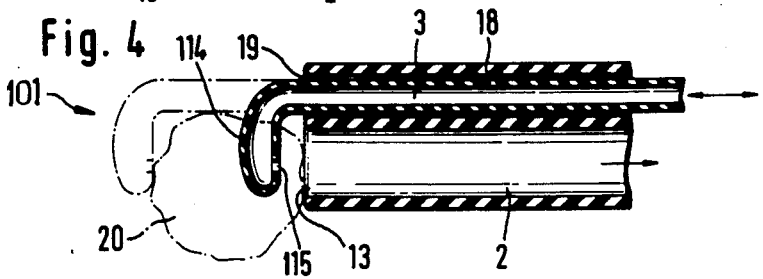
FIG. 4 is a view similar to FIG. 2 but illustrating another embodiment of the invention.

In FIG. 4, where similarly functioning elements are designated with similar reference numerals, the catheter 101 has a tongue 114 with a nozzle 115 formed at the end of a tube 18 guided in a passage 19 formed unitarily in the catheter, parallel to the suction duct 2 whose mouth is shown at 13.

In operation, the tube 18 is shifted to the left (FIG. 4) so that the thrombus or stone 20 can be received between the nozzle 115 and the mouth 13 of the catheter and thereby captured by the latter. The jet from nozzle 115 serves to break up the stone, the fragments passing from the duct 2 and being collected in the vessel 7. Larger fragments unable to pass freely through the suction duct 2 can be captured anew and in turn broken up until all traces of the stone are removed.

I claim:

1. An apparatus for the removal of a solid structure from a passage in a body of a patient, said apparatus comprising:
    a flexible dual duct catheter having distal and proximal ends adapted to be inserted into said passage and formed with
    a flexible suction duct means having an outer portion opening at an open mouth at the distal end of said catheter placed in fluid communication with the passage in the patient's body and of substantially uniform flow cross-section between the proximal and distal ends of said suction duct means,
    a flexible positive pressure duct means extending substantially along said outer portion of said suction duct means and terminating and extending distally of said mouth of said suction duct means and having a nozzle with an opening means to direct fluid in a direction opposite to the direction of flow in said positive pressure duct means into said open mouth at the distal end of said suction duct means, the positive pressure duct means being of substantially smaller flow cross section than the suction duct means, and
    a flexible wall extending along, unitary with and separating said suction duct means and pressure duct means laterally from each other, the wall adjacent said open mouth having a row of orifices extending longitudinally in the wall rearwardly from said open mouth providing fluid communication between said suction duct means and said pressure duct means;

means including a suction pump connected to said suction duct means at the porximal duct means end thereof remote from the suction-duct means mouth for aspirating material into and back through the suction duct means in an inward particle-flow direction; and means including a high-pressure pump connected to said pressure duct means remote from the nozzle thereof for pressurizing the pressure duct means and thereby simultaneously directing a stream of water from the nozzle back into the mouth of the suction duct means to break up a solid structure at the mouth and for directing respective streams of said fluid from the orifices back into said suction duct means in the particle flow direction.

* * * * *